US012773280B2

(12) United States Patent
Zucker et al.

(10) Patent No.: US 12,773,280 B2
(45) Date of Patent: Oct. 27, 2026

(54) SYSTEMS AND METHODS FOR DEFINING OBJECT GEOMETRY USING ROBOTIC ARMS

(71) Applicant: Mazor Robotics Ltd., Caesarea (IL)

(72) Inventors: Ido Zucker, Tel Aviv (IL); Avi Turgeman, Beer Yaakov (IL)

(73) Assignee: Mazor Robotics Ltd., Caesarea (IL)

(*) Notice: Subject to any disclaimer, the term of this patent is extended or adjusted under 35 U.S.C. 154(b) by 720 days.

(21) Appl. No.: 17/498,488

(22) Filed: Oct. 11, 2021

(65) Prior Publication Data

US 2023/0115849 A1 Apr. 13, 2023

(51) Int. Cl.

*A61B 17/70* (2006.01)
*A61B 34/30* (2016.01)
*A61B 90/00* (2016.01)
*A61B 34/20* (2016.01)

(52) U.S. Cl.

CPC .......... *A61B 34/30* (2016.02); *A61B 17/7011* (2013.01); *A61B 17/7083* (2013.01); *A61B 90/06* (2016.02); *A61B 2034/2057* (2016.02); *A61B 2090/061* (2016.02)

(58) Field of Classification Search

CPC ....... A61B 17/70–7046; A61B 17/7083–7092; A61B 34/30

See application file for complete search history.

(56) References Cited

U.S. PATENT DOCUMENTS 6,033,415 A 3/2000 Mittelstadt et al.
8,235,998 B2 * 8/2012 Miller ................ A61B 17/8863 606/86 A
9,414,859 B2 * 8/2016 Ballard .............. A61B 17/8863
10,405,935 B2 * 9/2019 Mcgahan ............... A61B 34/20
10,779,893 B2 * 9/2020 Elliott .................. A61B 90/361
10,849,691 B2 12/2020 Zucker et al.
11,065,065 B2 * 7/2021 Rezach .............. A61B 17/7082
2018/0147018 A1 * 5/2018 Crawford ........... A61B 17/7035
2018/0289408 A1 * 10/2018 McGahan .......... A61B 17/8863
2019/0021800 A1 * 1/2019 Crawford ............... A61B 6/547
2019/0038366 A1 * 2/2019 Johnson ................. A61B 90/98
2019/0090966 A1 * 3/2019 Kang ................. A61B 17/1671
2019/0231435 A1 * 8/2019 Zucker ............... A61B 17/7077
2019/0389065 A1 12/2019 Horiguchi et al.
2020/0070369 A1 3/2020 Son et al.
2020/0130961 A1 * 4/2020 Diankov ................. B65B 43/46
2020/0405375 A1 * 12/2020 Shelton, IV ....... A61B 18/1815
2021/0177603 A1 * 6/2021 Dewey ................... B33Y 80/00

OTHER PUBLICATIONS

International Search Report and Written Opinion for International (PCT) Patent Application No. PCT/IL2022/051059, dated Feb. 9, 2023, 14 pages.

* cited by examiner

*Primary Examiner* — Eduardo C Robert
*Assistant Examiner* — Steven J Cotroneo
(74) *Attorney, Agent, or Firm* — Sheridan Ross PC

(57) ABSTRACT

A system according to at least one embodiment of the present disclosure includes a processor; at least one robotic arm; and a memory storing data for processing by the processor that, when processed by the processor, cause the processor to: manipulate the at least one robotic arm when holding an object; and determine a configuration of the object based on a position of the at least one robotic arm and information describing another point of the object relative to the at least one robotic arm.

20 Claims, 8 Drawing Sheets

SYSTEMS AND METHODS FOR DEFINING OBJECT GEOMETRY USING ROBOTIC ARMS

FIELD

The present technology generally relates to defining object geometry, and relates more particularly to defining geometry with robotic assistance.

BACKGROUND

Surgical robots may assist a surgeon or other medical provider in carrying out a surgical procedure, or may complete one or more surgical procedures autonomously. Robotic arms may have end effectors that can hold an object. The object may be used during a surgery or surgical procedure.

SUMMARY

Example aspects of the present disclosure include:

A system according to at least one embodiment of the present disclosure comprises: a processor; at least one robotic arm; and a memory storing data for processing by the processor that, when processed by the processor, cause the processor to: manipulate the at least one robotic arm when holding an object; and determine a configuration of the object based on a position of the at least one robotic arm and information describing another point of the object relative to the at least one robotic arm.

Any of the aspects herein, wherein the processor further determines a contour of the object.

Any of the aspects herein, wherein the object comprises a rod.

Any of the aspects herein, wherein the rod is inserted between a first screw and a second screw.

Any of the aspects herein, wherein the information describing the another point of the object comprises a position of a first end of the rod.

Any of the aspects herein, wherein the at least one robotic arm grips the rod at a second end opposite the first end of the rod.

Any of the aspects herein, wherein the at least one robotic arm comprises a first arm and a second arm, and wherein the second arm is used, at least in part, to describe the another point of the object relative to the at least one robotic arm.

Any of the aspects herein, wherein the information describing the another point of the object comprises image data obtained from a first imaging device.

Any of the aspects herein, wherein the at least one robotic arm comprises a first navigation marker, and wherein the data further cause the processor to: determine, based on a movement of the first navigation marker relative to the object, a contour of the object.

A system according to at least one embodiment of the present disclosure comprises: a processor; a first robotic arm; a second robotic arm disposed proximate the first robotic arm; and a memory storing data for processing by the processor that, when processed by the processor, cause the processor to: cause the second robotic arm to move relative to the first robotic arm when the first robotic arm holds an object; and determine, based on the position of the first robotic arm and movement of the second robotic arm relative to the first robotic arm, a configuration of the object.

Any of the aspects herein, wherein the object comprises a rod.

Any of the aspects herein, wherein the system further comprises: a first tracking device, the first tracking device configured to track a position of a first navigation marker disposed on the second robotic arm.

Any of the aspects herein, wherein the configuration of the object is determined based at least in part on information related to a movement of the first navigation marker.

Any of the aspects herein, wherein the first navigation marker comprises an infrared emitting diode (IRED).

Any of the aspects herein, wherein the first tracking device comprises an infrared (IR) camera.

Any of the aspects herein, wherein an end effector of the second robotic arm moves along at least one of a first end of an object or along a first surface of the object toward the first robotic arm.

Any of the aspects herein, wherein the data further cause the processor to: determine, based on the movement of the second robotic arm, a contour of the object.

Any of the aspects herein, wherein the object is disposed with a first end threaded through a first screw and a second end threaded through a second screw.

A method according to at least one embodiment of the present disclosure comprises: receiving information describing a first pose of a first robotic arm and a first position of an object held by the first robotic arm; causing the first robotic arm to move from the first pose to a second pose; determining, based on the second pose, a second position of the object; and determining, based on the first position and the second position of the object, a configuration of the object.

Any of the aspects herein, wherein the information comprises image information captured by a first imaging device.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as X1-Xn, Y1-Ym, and Z1-Zo, the phrase is intended to refer to a single element selected from X, Y, and Z, a combination of elements selected from the same class (e.g., X1 and X2) as well as a combination of elements selected from two or more classes (e.g., Y1 and Zo).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present disclosure will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1:
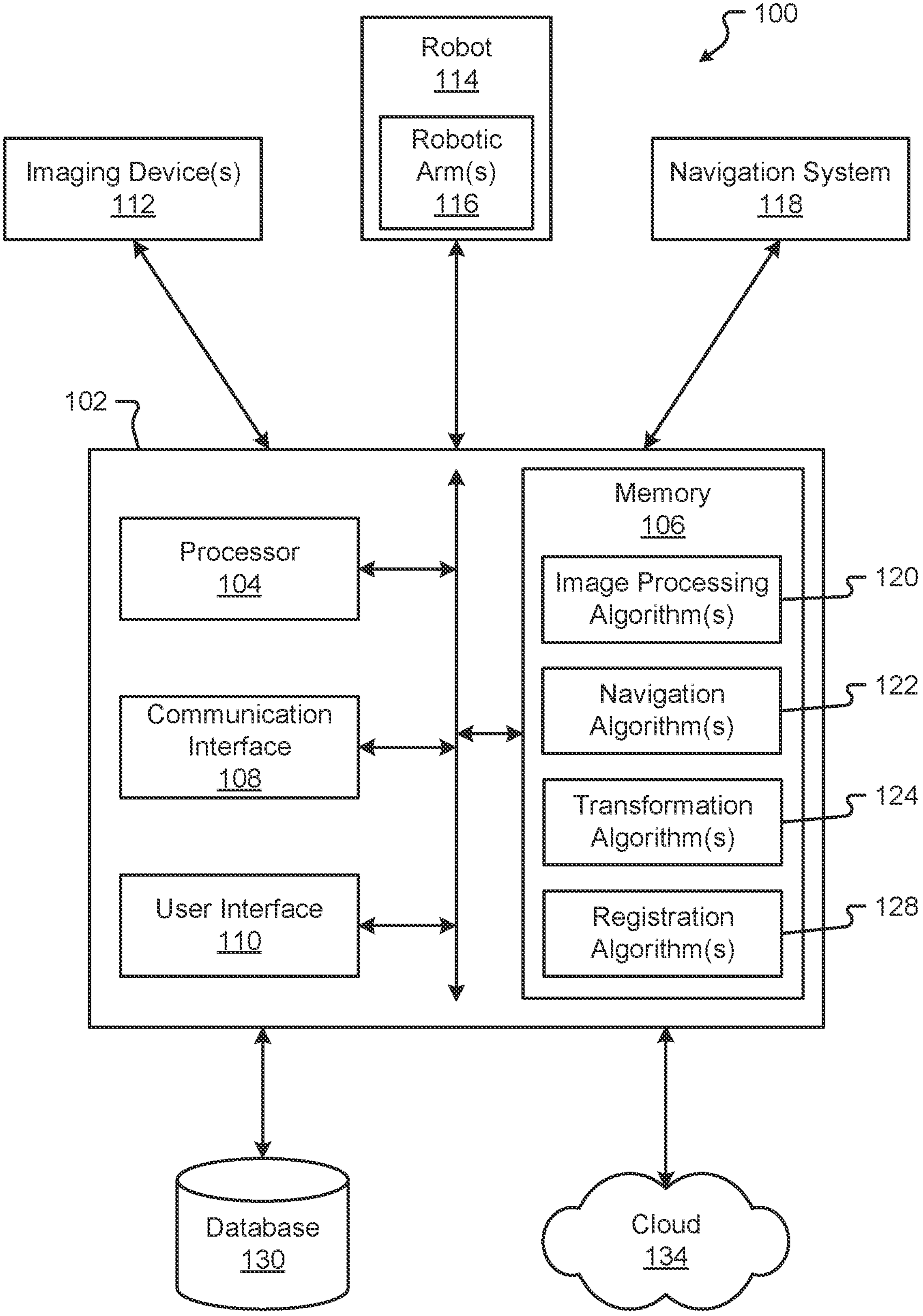
FIG. 1 is a block diagram of a system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Alternatively or additionally, functions may be implemented using machine learning models, neural networks, artificial neural networks, or combinations thereof (alone or in combination with instructions). Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The terms proximal and distal are used in this disclosure with their conventional medical meanings, proximal being closer to the operator or user of the system, and further from the region of surgical interest in or on the patient, and distal being closer to the region of surgical interest in or on the patient, and further from the operator or user of the system.

During some surgery or surgical procedures, such as spine fixation surgery, a rod may be used to connect one or more screws that have been inserted into patient anatomy (e.g., a vertebra). When the surgery or surgical procedure is performed using Minimal Invasive Surgery (MIS) techniques, inserting the rod between two or more screws may be more challenging than in non-MIS surgeries or surgical procedures. The rod may be held by a robotic arm, and the robotic arm may assist with positioning the rod to facilitate inserting the rod between the screws. A system may use registration techniques to define the position of the screws, but when inserting the rod (i.e., threading the rod through the screws), the head or tip of the rod may need to be defined in space or a common coordinate system with the screws and/or the patient anatomy. Sometimes, the rod may be reshaped or otherwise changed before the threading (e.g., a surgeon bends or reshapes the rod by hand), leading to possible pose and/or navigational issues when the robotic arm attempts to thread the rod through the screws.

Issues with the above may be addressed with embodiments of the disclosure presented herein. In accordance with embodiments of the present disclosure, the rod may be sampled via a robotic arm and a known position in space. By moving the robotic arm relative to the known position in space, the shape of the ends of the rod and/or the shape of the middle of the rod connecting the two ends of the rod may be determined. In accordance with embodiments of the present disclosure, a first robotic arm may hold the rod, and a second robotic arm may sample the tip or contour of the rod (e.g., the second robotic arm may move around or on the surface of the rod). The first robotic arm and the second robotic arm may be in or registered to the same coordinate system and/or may possess navigation markers to track the position and orientation of each robotic arm in reference to the other (and/or to the system).

In accordance with embodiments of the present disclosure, the first robotic arm may hold the rod at a first known position in space (e.g., known to one or more systems controlling the first robotic arm). The system may also define a second known position in space. The rod (which is gripped by the first robotic arm) may then be guided (e.g., by a user) to the second known position in space, with the difference in the pose of the robotic arm being used to define the rod.

In accordance with embodiments of the present disclosure, the first robotic arm may hold the rod, and the rod may be sampled using a navigation marker. For instance, the first robotic arm may be in a known position, and the marker may be moved along the rod to sample the position of the rod. In some embodiments, the position of the marker and the first robotic arm may be both tracked by a navigation system.

Embodiments of the present disclosure provide technical solutions to one or more of the problems of (1) using undefined objects with MIS or other surgical procedures, (2) threading rods through surgical screws, and (3) performing surgeries (e.g., spinal fusion surgeries) using undefined tools.

Turning first to FIG. 1, a block diagram of a system 100 according to at least one embodiment of the present disclosure is shown. The system 100 may be used to determine the pose, shape, configuration, and/or contour of an object (e.g., an object gripped by a robotic arm such as a rod); to navigate one or more surgical tools or components during the course of a surgery or surgical procedure; to capture images of a surgical environment; and/or carry out one or more other aspects of one or more of the methods disclosed herein. The system 100 comprises a computing device 102, one or more imaging devices 112, a robot 114, a navigation system 118, a database 130, and/or a cloud or other network 134. Systems according to other embodiments of the present disclosure may comprise more or fewer components than the system 100. For example, the system 100 may not include the imaging device 112, the robot 114, the navigation system 118, one or more components of the computing device 102, the database 130, and/or the cloud 134.

The computing device 102 comprises a processor 104, a memory 106, a communication interface 108, and a user interface 110. Computing devices according to other embodiments of the present disclosure may comprise more or fewer components than the computing device 102.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the imaging device 112, the robot 114, the navigation system 118, the database 130, and/or the cloud 134.

The memory 106 may be or comprise RAM, DRAM, SDRAM, other solid-state memory, any memory described herein, or any other tangible, non-transitory memory for storing computer-readable data and/or instructions. The memory 106 may store information or data useful for completing, for example, any step of the methods 300 and/or 400 described herein, or of any other methods. The memory 106 may store, for example, instructions and/or machine learning models that support one or more functions of the robot. For instance, the memory 106 may store content (e.g., instructions and/or machine learning models) that, when executed by the processor 104, enable image processing 120, navigation 122, transformation 124, and/or registration 128. Such content, if provided as an instruction, may, in some embodiments, be organized into one or more applications, modules, packages, layers, or engines. Alternatively or additionally, the memory 106 may store other types of content or data (e.g., machine learning models, artificial neural networks, deep neural networks, etc.) that can be processed by the processor 104 to carry out the various method and features described herein. Thus, although various contents of memory 106 may be described as instructions, it should be appreciated that functionality described herein can be achieved through use of instructions, algorithms, and/or machine learning models. The data, algorithms, and/or instructions may cause the processor 104 to manipulate data stored in the memory 106 and/or received from or via the imaging device 112, the robot 114, the database 130, and/or the cloud 134.

The computing device 102 may also comprise a communication interface 108. The communication interface 108 may be used for receiving image data or other information from an external source (such as the imaging device 112, the robot 114, the navigation system 118, the database 130, the cloud 134, and/or any other system or component not part of the system 100), and/or for transmitting instructions, images, or other information to an external system or device (e.g., another computing device 102, the imaging device 112, the robot 114, the navigation system 118, the database 130, the cloud 134, and/or any other system or component not part of the system 100). The communication interface 108 may comprise one or more wired interfaces (e.g., a USB port, an Ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 108 may be useful for enabling the device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, screen, touchscreen, and/or any other device for receiving information from a user and/or for providing information to a user. The user interface 110 may be used, for example, to receive a user selection or other user input regarding any step of any method described herein. Notwithstanding the foregoing, any required input for any step of any method described herein may be generated automatically by the system 100 (e.g., by the processor 104 or another component of the system 100) or received by the system 100 from a source external to the system 100. In some embodiments, the user interface 110 may be useful to allow a surgeon or other user to modify instructions to be executed by the processor 104 according to one or more embodiments of the present disclosure, and/or to modify or adjust a setting of other information displayed on the user interface 110 or corresponding thereto.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computer device 102.

The imaging device 112 may be operable to image anatomical feature(s) (e.g., a bone, veins, tissue, etc.) and/or other aspects of patient anatomy to yield image data (e.g., image data depicting or corresponding to a bone, veins, tissue, etc.). "Image data" as used herein refers to the data generated or captured by an imaging device 112, including in a machine-readable form, a graphical/visual form, and in any other form. In various examples, the image data may comprise data corresponding to an anatomical feature of a patient, or to a portion thereof. The image data may be or comprise a preoperative image, an intraoperative image, a postoperative image, or an image taken independently of any surgical procedure. In some embodiments, a first imaging device 112 may be used to obtain first image data (e.g., a first image) at a first time, and a second imaging device 112 may be used to obtain second image data (e.g., a second image) at a second time after the first time. The imaging device 112 may be capable of taking a 2D image or a 3D image to yield the image data. The imaging device 112 may be or comprise, for example, an ultrasound scanner (which may comprise, for example, a physically separate transducer and receiver, or a single ultrasound transceiver), an O-arm, a C-arm, a G-arm, or any other device utilizing X-ray-based imaging (e.g., a fluoroscope, a CT scanner, or other X-ray machine), a magnetic resonance imaging (MM) scanner, an optical coherence tomography (OCT) scanner, an endoscope, a microscope, an optical camera, a thermographic camera (e.g., an infrared camera), a radar system (which may comprise, for example, a transmitter, a receiver, a processor, and one or more antennae), or any other imaging device 112 suitable for obtaining images of an anatomical feature of a patient. The imaging device 112 may be contained entirely within a single housing, or may comprise a transmitter/emitter and a receiver/detector that are in separate housings or are otherwise physically separated. In some embodiments, the imaging devices 112 may capture images or image information of non-anatomic features, such as that of other objects within the surgical environment (e.g., robotic arms, objects held by the robotic arms, etc.).

In some embodiments, the imaging device 112 may comprise more than one imaging device 112. For example, a first imaging device may provide first image data and/or a first image, and a second imaging device may provide second image data and/or a second image. In still other embodiments, the same imaging device may be used to provide both the first image data and the second image data, and/or any other image data described herein. The imaging device 112 may be operable to generate a stream of image data. For example, the imaging device 112 may be configured to operate with an open shutter, or with a shutter that continuously alternates between open and shut so as to capture successive images. For purposes of the present disclosure, unless specified otherwise, image data may be considered to be continuous and/or provided as an image data stream if the image data represents two or more frames per second.

The robot 114 may be any surgical robot or surgical robotic system. The robot 114 may be or comprise, for example, the Mazor X™ Stealth Edition robotic guidance system. The robot 114 may be configured to position the imaging device 112 at one or more precise position(s) and orientation(s), and/or to return the imaging device 112 to the same position(s) and orientation(s) at a later point in time. The robot 114 may additionally or alternatively be configured to manipulate a surgical tool (whether based on guidance from the navigation system 118 or not) to accomplish or to assist with a surgical task. In some embodiments, the robot 114 may be configured to hold and/or manipulate an anatomical element during or in connection with a surgical procedure. The robot 114 may comprise one or more robotic arms 116. In some embodiments, the robotic arm 116 may comprise a first robotic arm and a second robotic arm, though the robot 114 may comprise more than two robotic arms. In some embodiments, one or more of the robotic arms 116 may be used to hold and/or maneuver the imaging device 112. In embodiments where the imaging device 112 comprises two or more physically separate components (e.g., a transmitter and receiver), one robotic arm 116 may hold one such component, and another robotic arm 116 may hold another such component. Each robotic arm 116 may be positionable independently of the other robotic arm. The robotic arms may be controlled in a single, shared coordinate space, or in separate coordinate spaces.

The robot 114, together with the robotic arm 116, may have, for example, one, two, three, four, five, six, seven, or more degrees of freedom. Further, the robotic arm 116 may be positioned or positionable in any pose, plane, and/or focal point. The pose includes a position and an orientation. As a result, an imaging device 112, surgical tool, or other object held by the robot 114 (or, more specifically, by the robotic arm 116) may be precisely positionable in one or more needed and specific positions and orientations.

The robotic arm(s) 116 may comprise one or more sensors that enable the processor 104 (or a processor of the robot 114) to determine a precise pose in space of the robotic arm (as well as any object or element held by or secured to the robotic arm).

In some embodiments, reference markers (i.e., navigation markers) may be placed on the robot 114 (including, e.g., on the robotic arm 116), the imaging device 112, or any other object in the surgical space (e.g., an object held by a robotic arm). The reference markers may be tracked by the navigation system 118, and the results of the tracking may be used by the robot 114 and/or by an operator of the system 100 or any component thereof. In some embodiments, the navigation system 118 can be used to track other components of the system (e.g., imaging device 112, robotic arms 116, objects held by the robotic arms 116, etc.) and the system can operate without the use of the robot 114 (e.g., with the surgeon manually manipulating the imaging device 112 and/or one or more surgical tools, based on information and/or instructions generated by the navigation system 118, for example).

The navigation system 118 may provide navigation for a surgeon and/or a surgical robot during an operation. The navigation system 118 may be any now-known or future-developed navigation system, including, for example, the Medtronic StealthStation™ S8 surgical navigation system or any successor thereof. The navigation system 118 may include one or more cameras or other sensor(s) for tracking one or more reference markers, navigated trackers, or other objects within the operating room or other room in which some or all of the system 100 is located. The one or more cameras may be optical cameras, infrared cameras, or other cameras. In some embodiments, the navigation system may comprise one or more electromagnetic sensors. In various embodiments, the navigation system 118 may be used to track a position and orientation (e.g., a pose) of the imaging device 112, the robot 114 and/or robotic arm 116, and/or one or more surgical tools (or, more particularly, to track a pose of a navigated tracker attached, directly or indirectly, in fixed relation to the one or more of the foregoing). The navigation system 118 may include a display for displaying one or more images from an external source (e.g., the computing device 102, imaging device 112, or other source) or for displaying an image and/or video stream from the one or more cameras or other sensors of the navigation system 118. In some embodiments, the system 100 can operate without the use of the navigation system 118. The navigation system 118 may be configured to provide guidance to a surgeon or other user of the system 100 or a component thereof, to the robot 114, or to any other element of the system 100 regarding, for example, a pose of one or more anatomical elements, whether or not a tool is in the proper trajectory, and/or how to move a tool into the proper trajectory to carry out a surgical task according to a preoperative or other surgical plan.

The database 130 may store information that correlates one coordinate system to another (e.g., one or more robotic coordinate systems to a patient coordinate system and/or to a navigation coordinate system). The database 130 may additionally or alternatively store, for example, one or more surgical plans (including, for example, pose information about a target and/or image information about a patient's anatomy at and/or proximate the surgical site, for use by the robot 114, the navigation system 118, and/or a user of the computing device 102 or of the system 100); one or more images useful in connection with a surgery to be completed by or with the assistance of one or more other components of the system 100; and/or any other useful information. The database 130 may be configured to provide any such information to the computing device 102 or to any other device of the system 100 or external to the system 100, whether directly or via the cloud 134. In some embodiments, the database 130 may be or comprise part of a hospital image storage system, such as a picture archiving and communication system (PACS), a health information system (HIS), and/or another system for collecting, storing, managing, and/or transmitting electronic medical records including image data.

The cloud 134 may be or represent the Internet or any other wide area network. The computing device 102 may be connected to the cloud 134 via the communication interface 108, using a wired connection, a wireless connection, or both. In some embodiments, the computing device 102 may communicate with the database 130 and/or an external device (e.g., a computing device) via the cloud 134.

The system 100 or similar systems may be used, for example, to carry out one or more aspects of any of the methods 300 and/or 400 described herein. The system 100 or similar systems may also be used for other purposes.

Figure 2A:
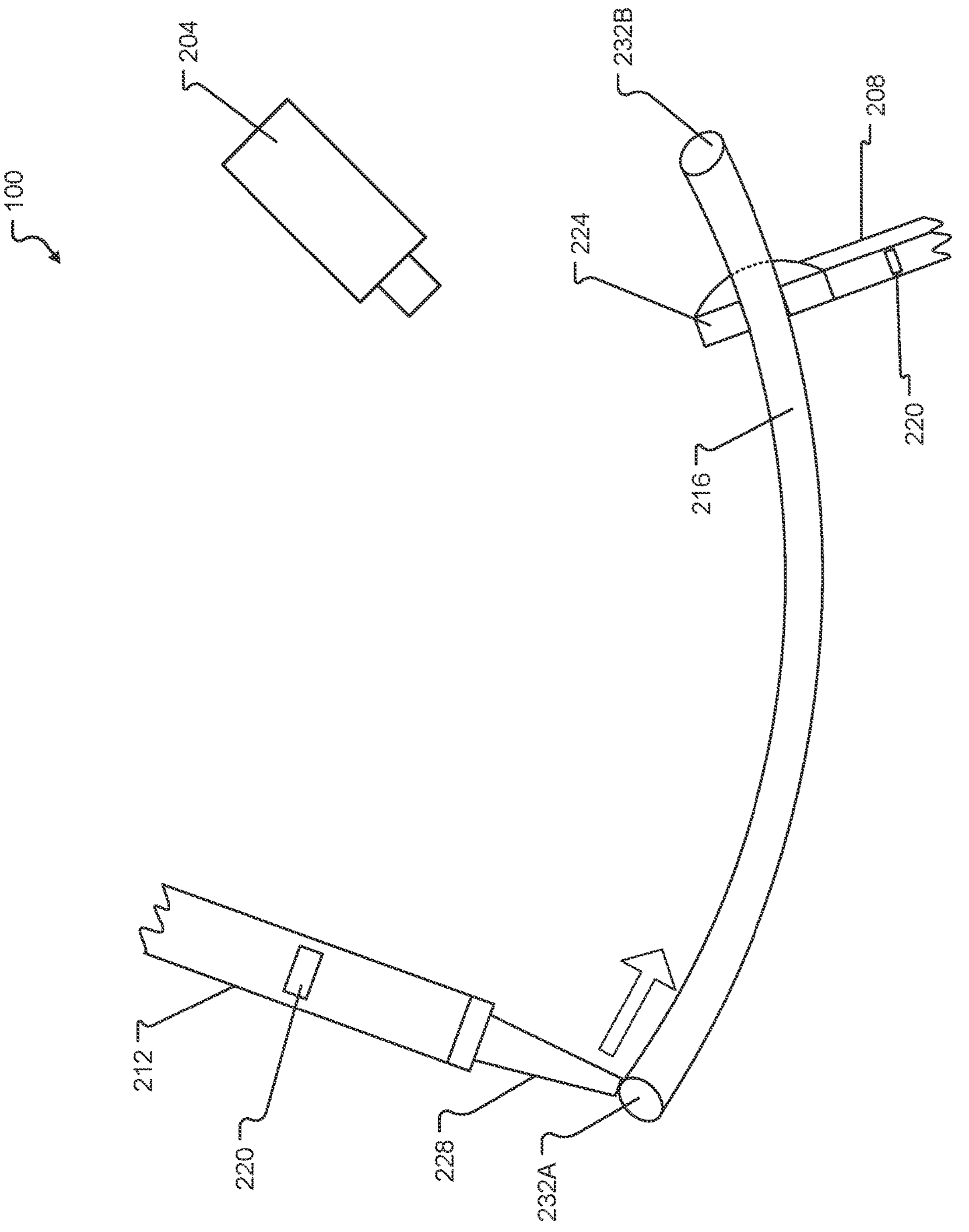
FIG. 2A is a diagram of robotic arms gripping an object according to at least one embodiment of the present disclosure.

FIG. 2A depicts aspects of the system 100 in accordance with at least one embodiment of the present disclosure. The system 100 comprises a navigation camera 204, a first robotic arm 208, a second robotic arm 212, and a rod 216. The navigation camera 204 may be an imaging device (e.g., an imaging device 112) or other tracking device (e.g., a navigation system such as the navigation system 118 and/or components thereof) configured to capture images or other image information related to the poses of the first robotic arm 208, the second robotic arm 212, and/or the rod 216.

In some embodiments, the navigation camera 204 may capture images or image information depicting one or more navigation markers 220. The navigation markers 220 may be disposed on one or more components of the system 100 (e.g., the first robotic arm 208, the second robotic arm 212, the rod 216, combinations thereof, and/or the like). As such, images or image information captured by the navigation camera 204 may allow the system 100 or one or more components thereof, such as the navigation system 118, to identify the navigation markers 220 (e.g., using an image processing algorithm 120 and/or a registration algorithm 128). The navigation system 118 may also determine, based on the pose of the navigation markers 220, the corresponding poses of the one or more components of the system 100 (such as the pose of the first robotic arm 208, the second robotic arm 212, the rod 216, combinations thereof, and/or the like). For example, the navigation markers 220 may be disposed in predetermined positions on the one or more components of the system 100 such that, by identifying the navigation markers 220 and using the predetermined positions, the system 100 can determine the poses of the one or more components of the system 100.

In some embodiments, the navigation markers 220 may provide, produce, or generate passive or active signals that can be detected by the navigation camera 204. In one embodiment, the navigation markers 220 may be or comprise Infrared Emitting Diodes (IREDs) that generate infrared signals. In such an embodiment, the navigation camera 204 may be or comprise an infrared camera configured to capture the signals generated by the IREDs and provide the captured signals (or information based on processing the signals) to the system 100 such that the system 100 can determine the pose of the IREDs and/or one or more components to which the IREDs are attached or affixed (e.g., robotic arms, surgical components or tools, etc.).

The first robotic arm 208 may be a robotic arm similar to or the same as other robotic arms described herein (e.g., a robotic arm 116 of a robot 114), and may be configured with or comprise a first end effector 224. The first end effector 224 may enable the first robotic arm 208 to grip, grab, attached to, or otherwise hold the rod 216. For example, the first end effector 224 may be or comprise a claw-like shape capable of wrapping around and gripping an outer surface of the rod 216. In some embodiments, the first end effector 224 may be or comprise components that fix or hold the rod 216 such that the rod 216 can move in a first direction but is prevented or limited in moving in a second direction. For instance, the first end effector 224 may be a hole through which the rod 216 is threaded, such that the rod 216 can move back and forth within the hole in a first direction but cannot move up or down and/or side to side in respective second and third directions. This may enable the system 100 to reduce the degrees of freedom of the rod 216 to better facilitate measurements associated with the rod 216 (such as determining an end point of the rod 216). In other embodiments, the first end effector 224 may grip the rod 216 such that the rod 216 is fixed with respect to the first end effector 224 (i.e., the rod 216 cannot move without the first end effector 224 moving as well, and vice versa).

The rod 216 may extend from a first end 232A and a second end 232B. The first end 232A may be an end of the rod 216 that is to be threaded through an area, slot, hole, or the like (e.g., a screw that has been inserted into a vertebra) during a surgery or surgical procedure by a robotic arm. As an example, the rod 216 may be used during the course of spinal surgery and is configured to be threaded through one or more screws that have been screwed into a vertebra. In some embodiments, the rod 216 may be threaded through the one or more screws autonomously or semi-autonomously by a robotic arm (e.g., first robotic arm 208). The second end 232B of the rod 216 may be an end of the rod 216 that is gripped by the first end effector 224 of the first robotic arm 208. In other embodiments, the first end 232A and the second end 232B may be reversed or flipped (i.e., the first end 232A may held by the first end effector 224 of the first robotic arm 208 while the second end 232B is threaded through a screw).

The second robotic arm 212 may comprise a second end effector 228. The second end effector 228 may be or comprise a tip or other contact point that contacts and/or traces one or more portions of the rod 216 (e.g., the first end 232A, the second end 232B, the portions of the rod 216 between the first end 232A and the second end 232B, etc.). In some embodiments, the second end effector 228 may be the similar to or the same as the first end effector 224. The movement of the second end effector 228 along, around, or relative to the rod 216 may enable the system 100 (or components thereof) to determine the shape, pose, and/or configuration of the rod 216.

The rod 216 may be gripped or held by the first end effector 224 of the first robotic arm 208, such that the rod 216 is fixed or has a known physical relationship relative to the first robotic arm 208. The first robotic arm 208 may comprise a navigation marker 220 that is tracked by the navigation camera 204, such that the pose of the first robotic arm 208 is known or can be determined by the system 100. In some embodiments, the first robotic arm 208 may remain fixed (e.g., the first robotic arm 208 may remain stationary and not move) while the second robotic arm 212 moves along surface(s) or the end(s) the rod 216. To determine the pose of the rod 216, the second end effector 228 may be caused to move (e.g., by controlling the motion of the second robotic arm 212 to which the second end effector 228 is connected) along the first end 232A, the second end 232B, the areas of the rod 216 therebetween, and/or any other portion of the rod 216. In some embodiments, the second end effector 228 may be aligned such that the starting position of the second end effector 228 on the rod 216 is known. For instance, the second robotic arm 212 may comprise a navigation marker 220, and the system 100 may determine the pose of the second robotic arm 212 using location the navigation marker 220 and/or predetermined information related to the position of the navigation marker 220 relative to the second robotic arm 212 and/or the second end effector 228. Furthermore, the second end effector 228 may be a fixed and known distance from the navigation marker 220 such that, by determining the pose of the second robotic arm 212, the system 100 also knows (or determines based on the known distance) the pose of the second end effector 228. The system 100 may cause the second robotic arm 212 to move such that the second end effector 228 moves along the rod 216. In some embodiments, the system 100 may make use of one or more navigation algorithms (e.g., navigation algorithms 122) that receive images or image information associated with the pose of the navigation markers 220 disposed on the second robotic arm 212, determine the pose of the second robotic arm 212, and cause the second robotic arm 212 to move based on the pose of the second robotic arm 212.

In some embodiments, the second end effector 228 may comprise one or more sensors (e.g., force sensors, inertial sensors, etc.) that provide readings when a portion of the second end effector 228 contacts or touches the rod 216. As such, the readings from the sensors may enable the system 100 to determine when movement of the second robotic arm 212 causes the second end effector 228 to contact and/or no longer contact the surface(s) or end(s) of the rod 216 (such as when the readings from the sensors no longer measure contact between the second end effector 228 and the rod 216). In some embodiments, when the second end effector 228 moves away from the rod 216 (such as when the rod 216 curves downward and the second end effector 228 continues in a straight line such that the second end effector 228 no longer contacts the rod 216), the system 100 may determine that the second end effector 228 no longer contacts the rod 216, and may cause the second robotic arm 212 to return to the last known pose where the second end effector 228 contacted the rod 216 (e.g., the pose of the second robotic arm 212 when the one or more sensors last registered contact between the second end effector 228 and the rod 216). The system 100 may cause a change in pose of the second robotic arm 212 such that the second end effector 228 moves in a different direction than before. In some embodiments, the system 100 may perform multiple pose changes to the second robotic arm 212 until the second end effector 228 contacts the rod 216 (which may occur when the one or more sensors begin providing measurements indicating contact between the second end effector 228 and the rod 216) to effectively trace and determine the boundaries of the rod 216.

In one embodiment, the first robotic arm 208 may grip the rod 216 at or near the second end 232B (e.g., within a predetermined proximity of the second end 232B), and the second robotic arm 212 may be in such a pose that the second end effector 228 contacts the rod 216 at or near the first end 232A (e.g., within a predetermined proximity of the first end 232A). The second robotic arm 212 may be caused to move along the surface of the rod 216 toward the first robotic arm 208. The second robotic arm 212 may continue along the surface of the rod 216 until the second end effector 228 contacts or moves within a threshold distance of the first end effector 224 of the first robotic arm 208. As the second end effector 228 moves along the surface(s) or end(s) of the rod 216, the navigation camera 204 may track the movements thereof (e.g., using navigation markers 220 positioned on the second robotic arm 212). In some embodiments, the second robotic arm 212 may be in such a pose that the second end effector 228 does not contact the first end 232A but is in a pose known by the system 100 (or components thereof). In such embodiments, a user (e.g., a surgeon) may move the second end effector 228 (and consequently the second robotic arm 212) to contact the first end 232A. In moving the second end effector 228, the pose of the second robotic arm 212 may change from a first pose to a second pose, which may be captured by the navigation camera 204 based on the movement of navigation markers 220 affixed to the second robotic arm 212. The system 100 may then determine, based on the change in pose, a location in space of the first end 232A.

In some embodiments, the first robotic arm 208 may grip the rod 216 at or near the second end 232B, and the second robotic arm 212 may be in a pose such that the second end effector 228 contacts the rod 216 at or near the first end effector 224. The second end effector 228 may then be moved (by causing the pose of the second robotic arm 212 to change) such that the second end effector 228 moves from the first end effector 224 to the first end 232A. Upon reaching the first end 232A, the system 100 may stop the movement of the second robotic arm 212 (such that the second end effector 228 remains at the first end 232A. In other embodiments, such as the embodiment depicted in FIG. 2D, the second end effector 228 of the second robotic arm 212 may comprise a navigation marker 220. The navigation marker 220 of the second end effector 228 may be tracked by the navigation camera 204 as the second end effector 228 is caused to move along the rod 216. In some embodiments, the second end effector 228 may be similar to or the same as the first end effector 224 (e.g., an effector with a claw-like structure capable of gripping, wrapping around, or otherwise attaching to the surface of the rod 216). As the second end effector 228 moves along the rod 216, the navigation camera 204 may track the location and the change in location of the navigation marker 220 of the second end effector 228.

In some embodiments, the first robotic arm 208 may grip the rod 216 at or near the second end 232B, and the second robotic arm 212 may be in a pose such that the second end effector 228 contacts the rod 216 at or near the first end 232A. The system 100 may then cause the second robotic arm 212 to change pose such that the second end effector 228 moves across, around, and/or along the first end 232A. For instance, the second end effector 228 may move helically around the first end 232A, such that a radius and/or end geometry of the first end 232A may be defined based on the movement of the second end effector 228. The contact and movement of the second end effector 228 with respect to the first end 232A may allow or enable the system 100 to determine the curvature, shape, configuration, and/or location of an endpoint of the first end 232A, which may beneficially facilitate the use of the rod 216 in the surgery or surgical procedure (e.g., knowing the radius of the first end 232A may allow the system 100 to determine whether or not the rod 216 will fit through one or more holes provided by a screw that has been screwed into a vertebra during the course of a spine surgery). In some embodiments, the second end effector 228 may comprise one or more navigation markers 220, such that the system 100 can determine the configuration, shape, curvature, and/or location of the first end 232A based on the movement of the second end effector 228 (in addition or alternatively to such determinations based on the movement of the second robotic arm 212).

The system 100 may receive images or image information captured by the navigation camera 204 and, using one or more algorithms (e.g., image processing algorithms 120 and/or registration algorithms 128) to determine the contour of the rod 216. For instance, the system 100 or one or more components thereof (e.g., a computing device 102, a processor 104, etc.) may receive the information generated by the navigation camera 204 (e.g., the pose of the navigation markers 220 at various times as the second robotic arm 212 moved along the rod 216 and/or portions thereof) and may use the algorithms to determine a set of points in space where the second end effector 228 contacted the rod 216. The set of points may be used to define the contour of the rod 216. Additionally or alternatively, the system 100 may receive information related to the first end 232A. Using the information, the system 100 may be able to determine the location, pose, and/or shape of the first end 232A relative to, for example, the second end 232B, the first robotic arm 208, the first end effector 224, the second robotic arm 212, the second end effector 228, combinations thereof, and/or the like. In some embodiments, the system 100 may update a surgical plan based on the determined location, pose, and/or shape of the first end 232A. For instance, the surgical plan may call for using screws with holes of a first radius. However, after the system 100 has determined the shape of the first end 232A and that, for example, the overall radius of the first end 232A is a second radius, the system 100 may compare the two radii and determine that screws with a larger radius and/or a different rod with a smaller radius should be used and may update the surgical plan accordingly.

While the aspects of the system 100 as shown in FIG. 2A depict the rod 216, it is to be understood that the rod 216 may be or comprise any other object (e.g., a screw, a device designed to be implanted, an interbody screw or other interbody element, a surgical tool, a surgical wire, an electrode, etc.) capable of being held by the first robotic arm 208 and/or the second robotic arm 212. The configuration, shape, and/or pose of the object may be determined in a similar or the same manner as the rod 216 discussed herein (e.g., using one or more robotic arms to move along surfaces of the object, moving the object held by a robotic arm from a first position to a second position, etc.).

Figure 2B:
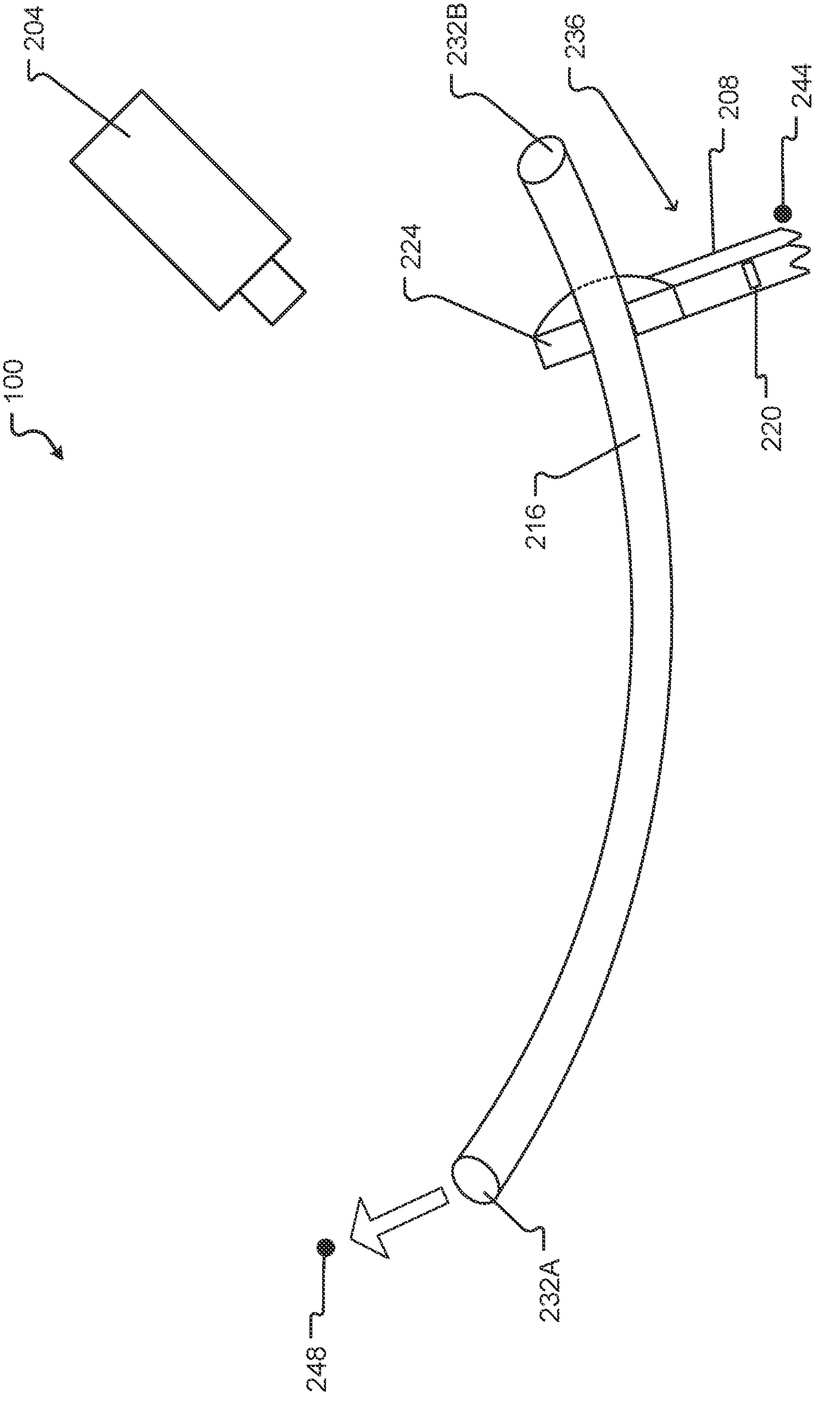
FIG. 2B shows a diagram of a movement of an object gripped by a robotic arm according to at least one embodiment of the present disclosure.
Figure 2C:
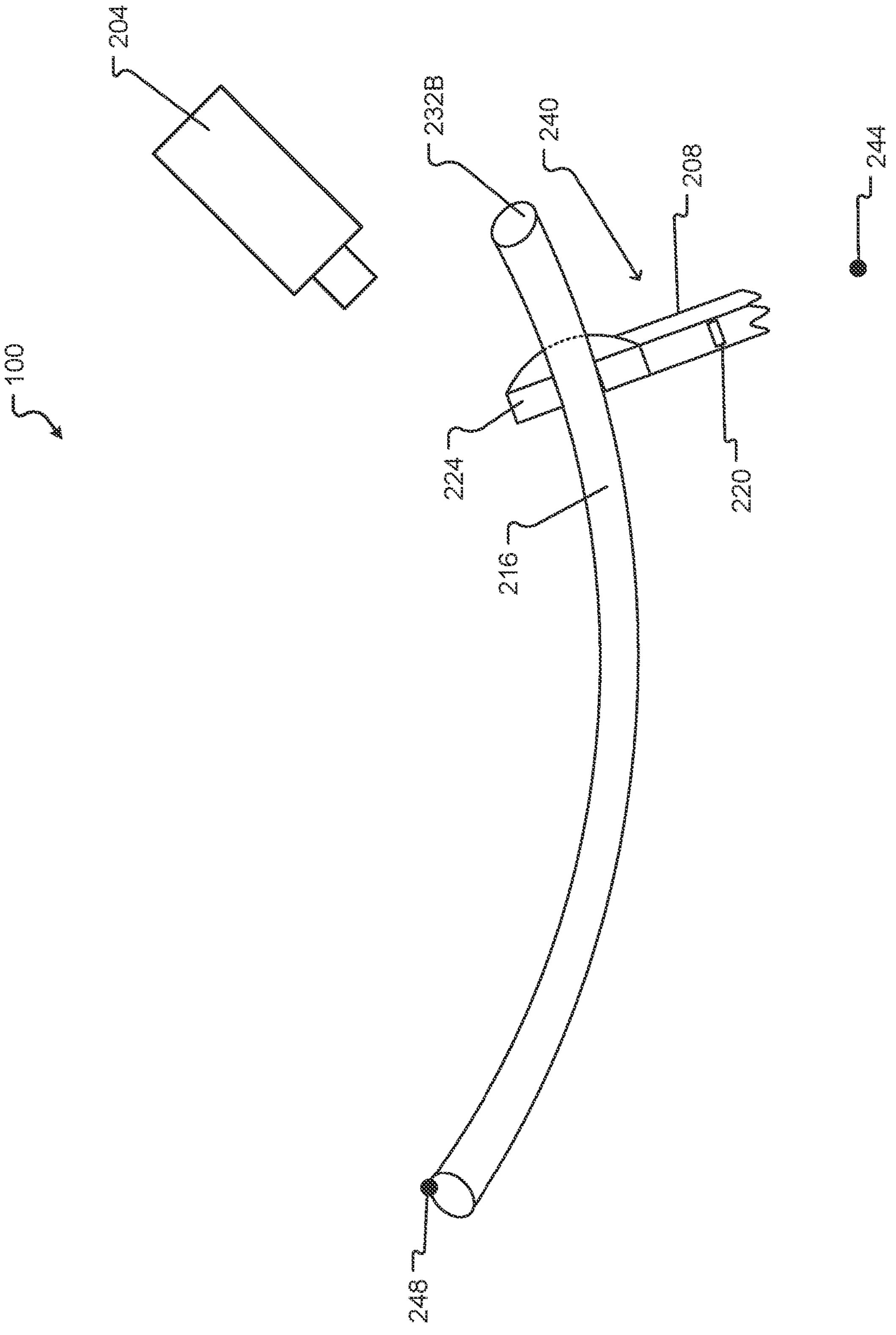
FIG. 2C shows a diagram of the object after the movement shown in FIG. 2B according to at least one embodiment of the present disclosure.
Figure 2D:
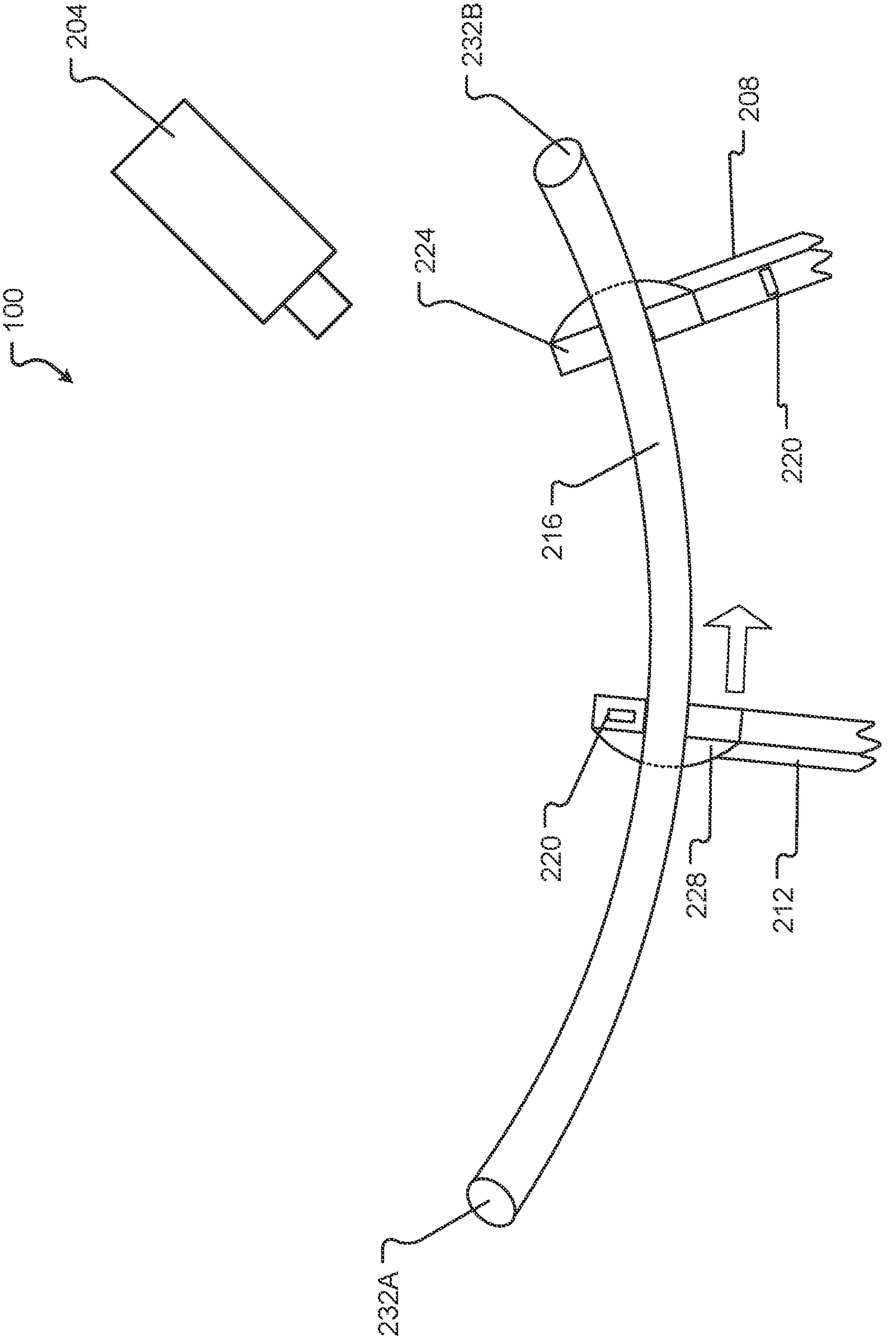
FIG. 2D shows a movement of a robotic arm along an object according to at least one embodiment of the present disclosure.

Additionally or alternatively, the rod 216 (and/or portions thereof) may be moved from a first pose to a second pose, such that the system 100 can track the change in pose and determine the configuration, contour, shape, and/or pose of the rod 216 (and/or the first end 232A and the second end 232B of the rod 216). As illustrated in FIG. 2B, the rod 216 may be gripped by the first robotic arm 208 at or near the second end 232B. The first robotic arm 208 may be in a first pose 236, which may be known by the system 100. Additionally or alternatively, the first robotic arm 208 may be positioned at a first position 244 that is known to the system 100. The system 100 may also have a second position 248 that is also known to the system 100. In some embodiments, the second position 248 may be a location that the system 100 has defined or identified (e.g., a corner of a surgical table, a location on a wall, a location on the floor, a location within a working volume, an area of a vertebra, a location on a screw inserted in a vertebra, etc.).

The first end 232A of the rod 216 (which may not be known by the system 100) may then be moved to the second position 248. In some embodiments, a user (e.g., a surgeon) may guide the first end 232A of the rod 216 to the second position 248. The first robotic arm 208 may be configured to respond to the movement of the rod 216, and the user may move the rod 216 such that the first end 232A is at the second position 248. For example, the second position 248 may be the top of a screw that has been inserted into a vertebra of a patient, and the user may move the first end 232A of the rod to the top of the screw. Once the first end 232A is at the second position 248, the system 100 may determine the pose of the first robotic arm 208. In moving the first end 232A to the second position 248, the first robotic arm 208 may move from the first pose 236 to a second pose 252. The navigation camera 204 may track the movement of the first robotic arm 208 (using a navigation marker 220 affixed to the first robotic arm 208, for example), and provide the tracking information to the system 100.

Based on the second pose 240 of the first robotic arm 208, the system 100 may determine a new position of the second end 232B. For instance, when in the first pose 236, the first robotic arm 208 may be a first distance away from the second end 232B (or, in some embodiments, gripping the rod 216 at the second end 232B), and the first pose 236 of the first robotic arm 208 may be defined based on the first position 244. As such, the second end 232B may be a predetermined distance away from the first position 244 (or the system 100 may determine the distance between the second end 232B and the first position 244 before the first robotic arm 208 moves from the first pose 236). After moving to the second pose 240, the system 100 may determine the distance between the second end 232B and the first position 244 based on the change in pose of the first robotic arm 208. The system 100 may use the determined distance to define the pose of the second end 232B.

The system 100 may proceed using the information about the new position of the second end 232B and the known position of the first end 232A at the second position 248 to define the configuration of the rod 216. In some embodiments, the system 100 may use one or more registration algorithms to define both the first end 232A and the second end 232B of the rod 216 by mapping coordinates associated with the first end 232A into a coordinate system associated with the second end 232B (or vice versa). In one embodiment, the registration algorithms may map both coordinates associated with the first end 232A and the second end 232B, as well as coordinates related to the pose of the first robotic arm 208, into a third coordinate system. In some embodiments, the configuration of the rod 216 may be or comprise the relative distances between the first end 232A and the second end 232B in one or more directions in 3D space. Since the locations of both the first end 232A and the second end 232B and the pose of the first robotic arm 208 are all expressed in a common coordinate system, the system 100 can navigate (e.g., using the navigation system 118) the first robotic arm 208 such that the first end 232A of the rod 216 is inserted correctly (e.g., the first end 232A is correctly positioned relative to one or more screw holes).

Figure 2E:
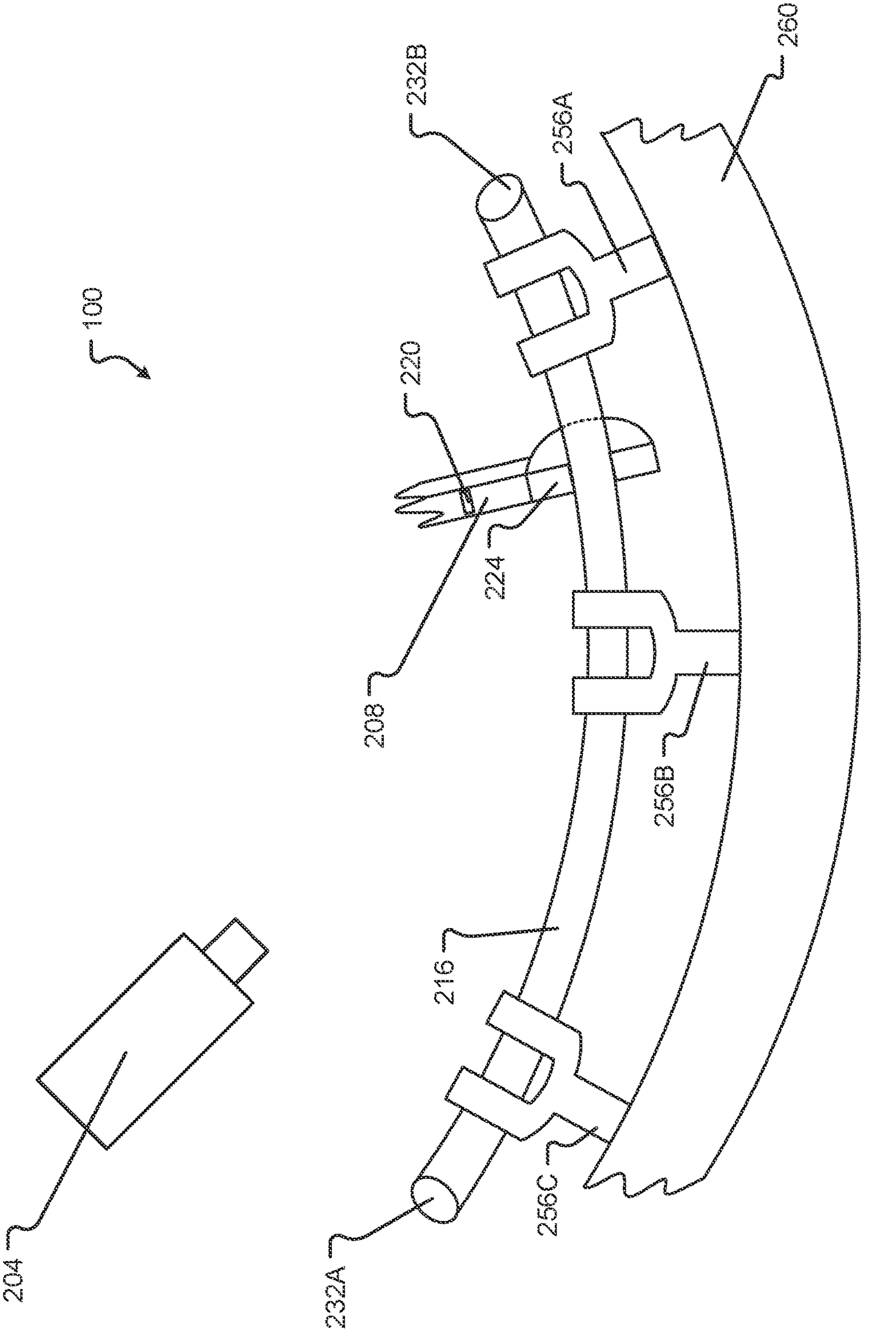
FIG. 2E depicts a robotic arm gripping a rod threaded through screws according to at least one embodiment of the present disclosure.

In some embodiments, after the system 100 has determined the configuration of the rod the rod 216 may be subsequently inserted (e.g., threaded) or otherwise used in a surgery or surgical procedure. As depicted in FIG. 2E, the rod 216 may be inserted into one or more holes of one or more screws 256A-256C. While the screws 256A-256C depict three screws, more or fewer screws may be present. Each of the screws 256A-256C may be screwed into a vertebra 260. The vertebra 260 may be a portion of the patient anatomy operated on by the surgeon during the surgery or surgical procedure. In some embodiments, the system 100 may use a surgical plan, along with information about the location of the first end 232A, to ensure that the rod 216 is threaded through the holes in the screws 256A-256C. For instance, the system 100 may use the surgical plan to identify the locations of the one or more holes of the screws 256A-256C, and use the information related to the position of the first end 232A relative to the first robotic arm 208 to determine the required movement of the first robotic arm 208 such that the first end 232A passes through the holes of the screws 256A-256C.

In some embodiments, the system 100 may use information gathered from the navigation camera 204 to cause the first robotic arm 208 to move such that the rod 216 is inserted between the screws 256A-256C. For example, the navigation marker 220 on the first robotic arm 208 may provide the navigation camera 204 with information related to the pose of the first robotic arm 208 (or the system 100 may determine the pose of the first robotic arm 208 based on measurements provided by the navigation marker 220). The system 100 may also know the configuration of the rod 216 (e.g., the locations of the first end 232A and/or the second end 232B relative to the first robotic arm 208), such that the system 100 can determine pose changes of the first robotic arm 208 to cause the first robotic arm 208 to move such that the rod 216 is threaded through the holes in the screws 256A-256C.

Figure 3:
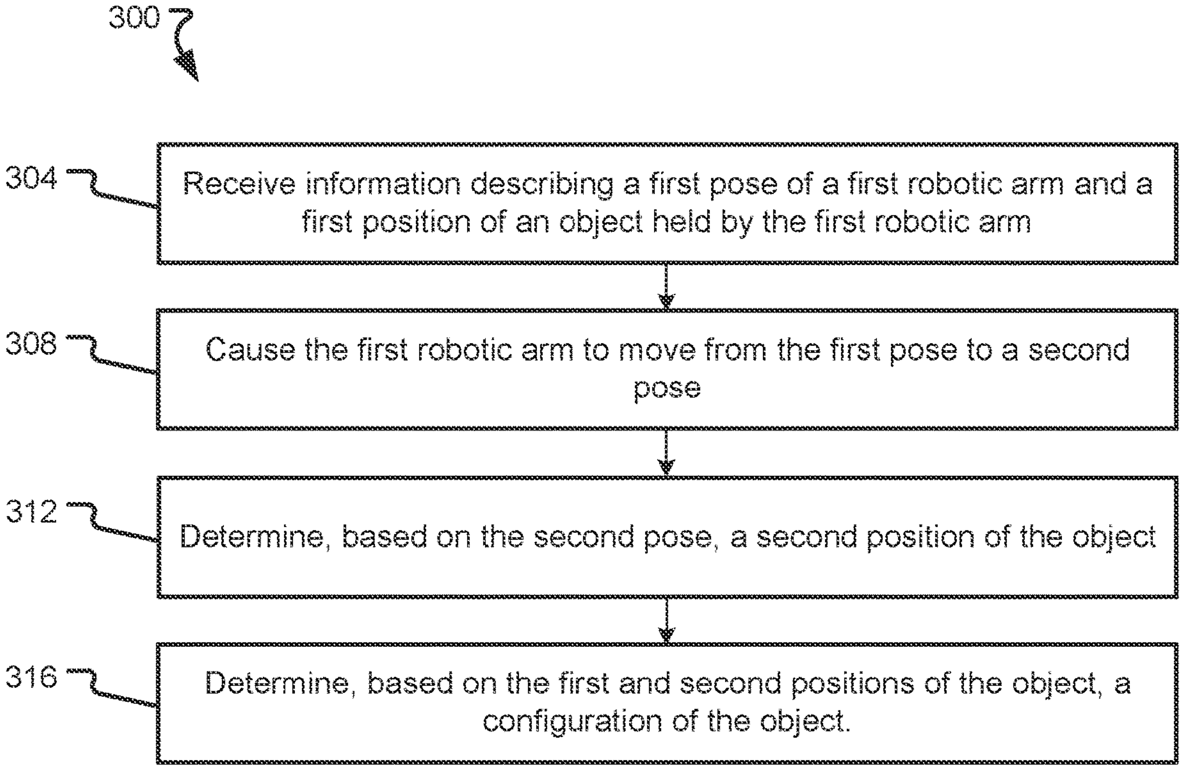
FIG. 3 is a flowchart according to at least one embodiment of the present disclosure.

FIG. 3 depicts a method 300 that may be used, for example, to determine a configuration of an object held or gripped by a robot or robotic arm.

One or more steps of the method 300 may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 300. The at least one processor may perform the method 300 by executing elements stored in a memory such as the memory 106. The elements stored in memory and executed by the processor may cause the processor to execute one or more steps of a function as shown in method 300. One or more portions of method 300 may be performed by the processor executing any of the contents of memory such as an image processing 120, a navigation 122, a transformation 124, and/or a registration 128.

The method 300 comprises receiving information describing a first pose of a first robotic arm and a first position of an object held by the first robotic arm (step 304). The information may be generated based on images or image information captured by a navigation camera (e.g., a navigation camera 204) of an object (e.g., a rod 216, a screw, a device designed to be implanted in patient anatomy, an interbody screw or other interbody element, a surgical tool, a surgical wire, an electrode, etc.) held by a first robotic arm (e.g., a first robotic arm 208). In some embodiments, the first position of the object may be the position of the object when held by the robotic arm before a surgery or surgical procedure (e.g., preoperatively). In other embodiments, the first position may be the position of the object after the object has been altered or otherwise manipulated during the course of a surgery or surgical procedure (e.g., the object may be a rod that has been bent by a surgeon before the rod is inserted between two screws). In such embodiments, the images or image information may be captured (e.g., by the navigation camera) before the object is inserted, with the images or image information being used by a system to determine the configuration, pose, and/or shape of the object.

The method 300 also comprises causing the first robotic arm to move from the first pose to a second pose (step 308). The step 308 may be implemented by the system to facilitate the determination of the configuration, pose, and/or shape of the object depicted in the images or image information of the step 304. In some embodiments, the system may know both the first pose and the second pose, and may cause the first robotic arm to move from the first pose to the second pose. In other embodiments, the change in pose of the first robotic arm may be controlled by components of other systems and/or by a user (e.g., a surgeon). In such embodiments, the movement of the first robotic arm may be captured by the navigation camera (e.g., by capturing images or image information that depicts the movement or change in pose of navigation markers attached to the first robotic arm), such that the system can determine the second pose of the first robotic arm.

The method 300 also comprises determining, based on the second pose, a second position of the object (step 312). As the first robotic arm moves from the first pose to the second pose, the navigation camera may capture images or image information related to the change in pose (e.g., by capturing images or image information that depicts the movement or change in pose of navigation markers attached to the first robotic arm), such that the system can determine the pose of one or more portions of the object held by the robot. For instance, the system may determine, based on the images or image information related to the second pose of the first robotic arm, that the object has moved from a first position to a second position, and that one or more ends of the object (e.g., a first end 232A and/or a second end 232B) have moved from a respective first position to a second position. In some embodiments, the step 308 may use or implement one or more image processing algorithms (e.g., image processing algorithms 120) that receive the images or image information as inputs, and output coordinates associated with the object.

In some embodiments, the movement of the first robotic arm from the first pose to the second pose may correspond to a movement of the object from the first position to a second position. For instance, the object may be fixed relative to the first robotic arm and, as such, any movement of the first robotic arm may correspond to the same movement of the object. The system may use one or more algorithms that receive the first and second poses of the first robotic arm, as well as a difference in pose between the object and the first pose of the first robotic arm, as inputs and output the second position of the object. For instance, a first end of the object may be gripped by the robotic arm, and when the robotic arm moves from the first pose to the second pose, the second end of the object may move to a known position (e.g., contacting a sensor, contacting a location in a working volume, etc.). As such, the system may determine a location of both the first end of the object (based on the known position), as well as the second end of the object (based on the change in pose of the robotic arm and the relative position of the second end of the object to the robotic arm).

The method 300 also comprises determining, based on the first and second positions of the object, a configuration of the object (step 316). The configuration of the object may be based on the location of the first end of the object relative to the second end of the object. For instance, the object may be a rod, and the configuration may be the distance between the first end of the rod and the second end of the rod in one or more directions. In some embodiments, the configuration of the object may comprise determining the shape or curvature of the object between the two ends. In some embodiments, the configuration of the object may be determined additional or alternative information captured by the system. For instance, the information may be related to images or image information captured by the navigation camera depicting the location of the first end of the object relative to a known location (e.g., a known location of a navigation marker). In such embodiments, system may implement one or more image processing algorithms (e.g., image processing algorithms 120) that receive the image of the navigation marker and the first end of the object and determine a relative distance between the first end of the object and the navigation marker and/or coordinates associated with the first end of the object. The system may also use one or more registration algorithms to convert the coordinates associated with the first end of the object into a different coordinate system (e.g., a coordinate system associated with the patient, a coordinate system associated with the robotic arm, etc.) such that the first end of the object is defined with respect to the robotic arm and/or the patient. The coordinates associated with the first end may then be used, along with coordinates associated with the second end of the object, to define a configuration of the object.

The present disclosure encompasses embodiments of the method 300 that comprise more or fewer steps than those described above, and/or one or more steps that are different than the steps described above.

Figure 4:
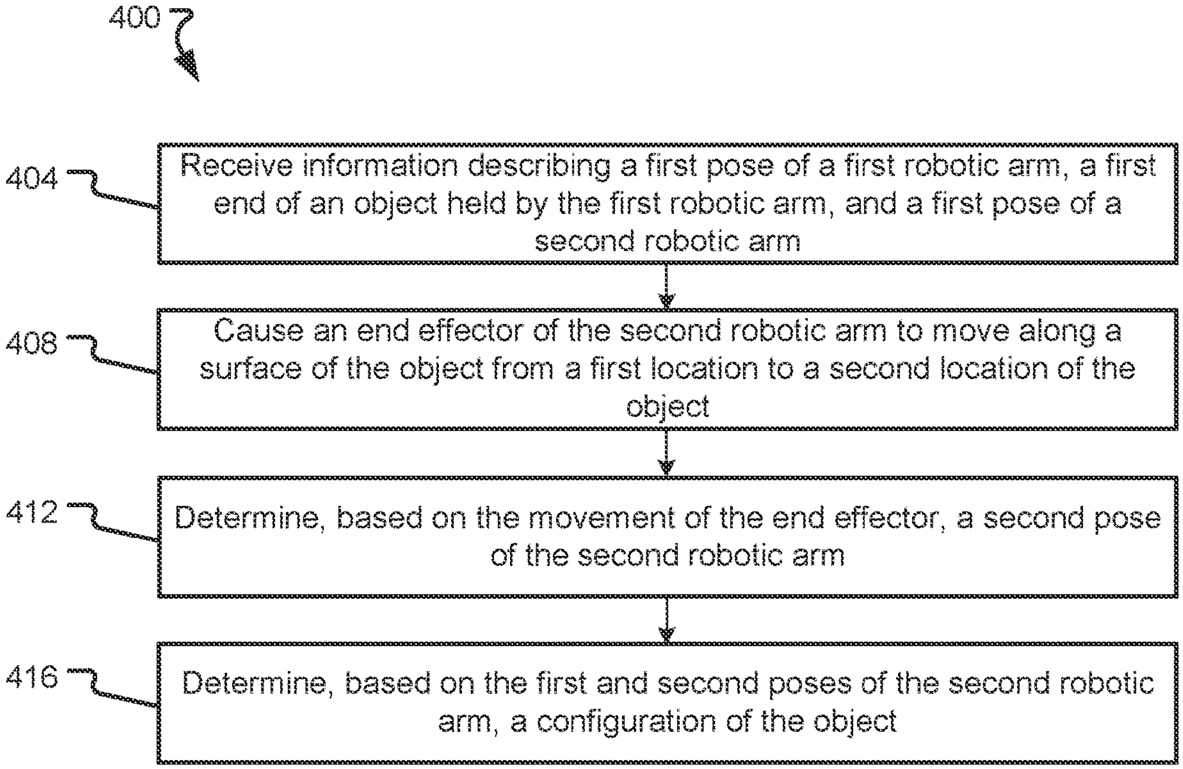
FIG. 4 is a flowchart according to at least one embodiment of the present disclosure.

FIG. 4 depicts a method 400 that may be used, for example, to determine a configuration of an object based on movements of robotic arms.

The method 400 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 400. The at least one processor may perform the method 400 by executing instructions stored in a memory such as the memory 106. The instructions may correspond to one or more steps of the method 400 described below. The instructions may cause the processor to execute one or more algorithms, such as an image processing algorithm 120, a navigation algorithm 122, a transformation algorithm 124, and/or a registration algorithm 128.

The method 400 comprises receiving information describing a first pose of a first robotic arm, a first end of an object held by the first robotic arm, and a first pose of a second robotic arm (step 404). The step 404 may be similar to or the same as the step 304 as discussed above with reference to the method 300. In some embodiments, the information may be or comprise coordinates associated with each of the first robotic arm, the second robotic arm, the first end of the object, one or more components thereof, combinations thereof, and/or the like.

The method 400 also comprises causing an end effector of the second robotic arm to move along a surface of the object from a first location to a second location of the object (step 408). The end effector of the second robotic arm may be disposed on the object (e.g., a rod), such that movement along the surface of the object traces the surface of the object from the first location of the object to the second location of the object. The first location may be a location on the object that lies between the first end of the object and a second end of the object. In one embodiment, the first location may be the same as the first end of the object and the second location may be a second end of the object (i.e., the end effector moves from the first end of the object to the second end of the object). The first end of the object may be held by an end effector of the first robotic arm and in a fixed position relative to the end effector and/or the first robotic arm, such that the first robotic arm and end effector move with the object and vice versa. In some embodiments, the end effector may move along just a second end of the object (e.g., the first location and the second location are both located on the second end of the object). The second end may be the furthest point from the first end of the object that is gripped by the first robotic arm.

The method 400 also comprises determining, based on the movement of the end effector, a second pose of the second robotic arm (step 412). The second pose of the second robotic arm may be determined based on images or image information captured by the navigation camera. For instance, as the end effector moves along the surface of the object, the second robotic arm may move with the end effector. Navigation markers disposed on or proximate the second robotic arm may be captured in the images or image information, and may be used by the system (e.g., using one or more image processing algorithms) to determine the movement and/or the second pose of the robotic arm.

In some embodiments, the multiple poses of the second robotic arm may be determined as the end effector moves along the object. For instance, the object may be or comprise a rod, and the end effector may trace around the circumference of a second end of the rod. In such embodiments, the pose of the second robotic arm may be determined as the end effector moves along the circumference of the second end of the rod. The pose determinations may be based on different intervals of time (e.g., every 0.1 seconds (s), every 0.2 s, every 0.5 s, every 1.5 s, every 2 s, etc.), such that shorter time intervals may result in additional data related to the shape of the first end of the rod.

The method 400 also comprises determining, based on the first pose and the second pose of the second robotic arm, a configuration of the object (step 416). The system may use one or more registration algorithms (e.g., registration algorithms 128) to determine the difference between the first pose and the second pose of the second robotic arm. The difference in poses may be or comprise the difference between coordinates associated with the second robotic arm in the first pose and coordinates associated with the second robotic arm in the second pose. The system may use the difference in coordinates to determine the configuration of the object. For example, the difference in coordinates between the poses of the second robotic arm may correspond to the same difference in coordinates associated with the first location of the object and the second location of the object (which may be the respective start and end locations of the end effector on the surface of the object). The configuration may be defined as the distance between the coordinates of the first location and the second location, such that the system knows both the first location of the object and the second location of the object.

In some embodiments, for instance where the end effector traces the circumference (or, more generally, the second end) of the rod, the navigation camera may capture multiple poses of the second robotic arms, and the configuration of the rod may be based on the captured poses. For instance, the system may compare, using one or more image processing algorithms, each of the multiple poses to the first pose of the second robotic arm, such that coordinates associated with each of the multiple poses is determined. The coordinates of the multiple poses may be used to determine coordinates associated with the second end of the rod; the system may use a known distance between the navigation markers and the end effector (which contacts the second end of the rod) to determine coordinates associated with the second end of the rod.

The system may, using one or more registration algorithms, map each of the coordinates into a common coordinate system (e.g., a coordinate system associated with the patient). In some embodiments, the system may determine (using, for example, one or more transformation algorithms such as transformation algorithms 124) additional information based on the coordinates of the second end. For instance, the transformation algorithms may interpolate between the coordinates associated with the second end of the rod (e.g., to determine coordinates defining the circumference of the second end of the rod). The determined circumference may be used by the system, for example, when navigating the first robotic arm to use the rod in the context of the surgery or surgical procedure (e.g., threading the rod through one or more surgical screws).

The present disclosure encompasses embodiments of the method 400 that comprise more or fewer steps than those described above, and/or one or more steps that are different than the steps described above.

As noted above, the present disclosure encompasses methods with fewer than all of the steps identified in FIGS. 3 and 4 (and the corresponding description of the methods 300 and 400), as well as methods that include additional steps beyond those identified in FIGS. 3 and 4 (and the corresponding description of the methods 300 and 400). The present disclosure also encompasses methods that comprise one or more steps from one method described herein, and one or more steps from another method described herein. Any correlation described herein may be or comprise a registration or any other correlation.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A system, comprising:

a processor;

a robotic arm; and a memory storing data for processing by the processor that, when processed by the processor, enable the processor to:

determine a first pose into which the robotic arm is to be maneuvered;

cause the robotic arm to move into the first pose, wherein an object held by the robotic arm is moved by the robotic arm as the robotic arm moves into the first pose;

manipulate a second robotic arm to move along a surface of the object and relative to the robotic arm while the robotic arm holds the object;

track, as the second robotic arm moves along the surface of the object, a movement of the second robotic arm; and determine a configuration of the object based on the first pose of the robotic arm and the tracked movement of the second robotic arm along the surface of the object and relative to the robotic arm.

2. The system of claim 1, wherein the processor further determines a contour of the object.

3. The system of claim 1, wherein the object comprises a rod.

4. The system of claim 3, wherein the rod is inserted between a first screw and a second screw.

5. The system of claim 4, wherein the first pose of the robotic arm comprises a position of a first end of the rod.

6. The system of claim 5, wherein the robotic arm grips the rod at the first end, and wherein the second robotic arm moves along a surface of a second end of the rod opposite the first end of the rod.

7. The system of claim 1, wherein the movement of the second robotic arm along the surface of the object is tracked by a first imaging device, and wherein tracking the movement of the second robotic arm comprises determining a second pose of the second robotic arm at predetermined time intervals as the second robotic arm moves along the surface of the object toward the robotic arm.

8. The system of claim 1, wherein the second robotic arm comprises a first navigation marker, and wherein the data further enable the processor to:

determine, based on a movement of the first navigation marker relative to the object, a contour of the object.

9. The system of claim 1, wherein the object comprises a rod, wherein the robotic arm holds a first end of the rod, and wherein the second robotic arm moves along a surface of a second end of the rod and toward the robotic arm.

10. A system, comprising:

a processor;

a first robotic arm;

a second robotic arm separate from and positioned proximate to the first robotic arm; and a memory storing data for processing by the processor that, when processed by the processor, enable the processor to:

determine a first pose into which the first robotic arm is to be maneuvered;

cause the first robotic arm to move into the first pose, wherein an object held by the first robotic arm is moved by the first robotic arm as the first robotic arm moves into the first pose;

cause the second robotic arm to move along a surface of the object and relative to the first robotic arm while the first robotic arm holds the object;

track, as the second robotic arm moves along the surface of the object, a movement of the second robotic arm; and determine, based on the first pose of the first robotic arm and the tracked movement of the second robotic arm along the surface of the object and relative to the first robotic arm, a configuration of the object.

11. The system of claim 10, wherein the object comprises a rod.

12. The system of claim 10, wherein the system further comprises:

a first tracking device, the first tracking device configured to track a position of a first navigation marker positioned on the second robotic arm.

13. The system of claim 12, wherein the configuration of the object is determined based at least in part on information related to a movement of the first navigation marker.

14. The system of claim 12, wherein the first navigation marker comprises an infrared emitting diode (IRED).

15. The system of claim 14, wherein the first tracking device comprises an infrared (IR) camera.

16. The system of claim 10, wherein an end effector of the second robotic arm moves along a first end of the object.

17. The system of claim 16, wherein the data further enable the processor to:

determine, based on the movement of the second robotic arm along the first end of the object, a contour of the first end of the object.

18. The system of claim 10, wherein the object is positioned with a first end threaded through a first screw and a second end threaded through a second screw.

19. A method, comprising:

determining a first pose into which a first robotic arm is to be maneuvered;

causing the first robotic arm to move into the first pose, wherein an object held by the first robotic arm is moved by the first robotic arm as the first robotic arm moves into the first pose;

causing a second robotic arm to move along a surface of the object and relative to the first robotic arm while the first robotic arm holds the object;

tracking, as the second robotic arm moves along the surface of the object, a movement of the second robotic arm; and determining, based on the first pose and the tracked movement of the second robotic arm along the surface of the object and relative to the first robotic arm, a configuration of the object.

20. The method of claim 19, wherein the object remains fixed relative to the first robotic arm as the second robotic arm moves along the surface of the object.

* * * * *